US00PP36059P2

(12) United States Plant Patent
Zaiger et al.

(10) Patent No.: US PP36,059 P2
(45) Date of Patent: Aug. 6, 2024

(54) NECTARINE TREE NAMED 'Flavor Fire'

(50) Latin Name: ***Prunus persica* var. *nucipersica***
Varietal Denomination: Flavor Fire

(71) Applicants: Gary Neil Zaiger, Modesto, CA (US); Leith Marie Gardner, Modesto, CA (US)

(72) Inventors: Gary Neil Zaiger, Modesto, CA (US); Leith Marie Gardner, Modesto, CA (US)

( * ) Notice: Subject to any disclaimer, the term of this patent is extended or adjusted under 35 U.S.C. 154(b) by 0 days.

(21) Appl. No.: 18/445,744

(22) Filed: Jan. 12, 2024

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
CPC ..... A01H 5/0856
See application file for complete search history.

*Primary Examiner* — Kent L Bell

(57) ABSTRACT

A new and distinct variety of nectarine tree. The following features of the tree and its fruit are characterized with the tree budded on 'Nemaguard' Rootstock (non-patented) , grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Fruit with an attractive red skin color.
4. Fruit having good flavor and eating quality.
5. Fruit with good storage and shipping ability.

1 Drawing Sheet

Botanical designation: *Prunus persica* var. *nucipersica*.
Variety denomination: 'Flavor Fire'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, California.

PRIOR VARIETIES

Among the existing varieties of nectarine trees, which are known to us, and mentioned herein, 'Honey Royale' Nectarine (U.S. Plant Pat. No. 12,008) , 'Red Ryan' Nectarine (U.S. Plant Pat. No. 19,588) and our proprietary non-patented nectarine seedling selections '27B554', '265BC180', '56ZE1030' and '18B280'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, California from a first generation cross between our proprietary non-patented nectarine seedling selections '27B554' and '265BC180'. The seed parent '27B554' originated from a first generation cross between 'Honey Royale' Nectarine (U.S. Plant Pat. No. 12,008) and our proprietary nectarine seedling selection '56ZE1030'. The pollen parent '265BC180' originated as an open pollinated seedling selection from the proprietary non-patented nectarine seedling '18B280'. A large number of these first generation seedlings were planted and grown on their own root system during which time we recognized the desirable tree and fruit characteristics of the present seedling and selected it in 2017 for additional asexual propagation and commercialization.

ASEXUAL REPRODUCTION OF THE VARIETY

In 2017 asexual reproduction of the new and distinct variety of nectarine tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding asexual propagations.

SUMMARY OF THE NEW VARIETY

The present new and distinct variety of nectarine tree (*Prunus persica* var. *nucipersica*) is of large size, vigorous, upright growth and a regular and productive bearer of large size, yellow flesh, clingstone fruit with good flavor and eating quality. The fruit is further characterized by its firm flesh and an attractive red skin color. In comparison to its proprietary non-patented nectarine seed parent '27B554' the fruit of the new variety is approximately 29 days earlier in maturity. In comparison to its proprietary non-patented nectarine pollen parent '265BC180' the fruit of the new variety is approximately 17 days earlier in maturity. In comparison to the commercial variety 'Red Ryan' Nectarine (U.S. Plant Pat. No. 19,588) the fruit of the new variety is approximately 5 days later in maturity and is larger in size.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 6 year old specimens grown near Modesto, California, with color in accordance with Munsell Book of Color published in 1958.

Tree:

*Size.*—Large, pruned to 3 to 3.5 meters in height and width for economical harvesting of fruit. Varies with different cultural practices.

*Vigor.*—Vigorous, tree growth of 1.5 to 2 meters the first growing season. Varies with cultural practices, soil type, fertility and climatic conditions.

*Form.*—Upright, usually pruned to vase shape.

*Branching habit.*—Upright, crotch angle approximately 30°, increases with heavy crop load.

*Productivity.*—Productive, thinning and spacing of fruit necessary for desired market size fruit. Number of fruit set varies with climatic conditions during blooming period.

*Bearer.*—Regular, has had adequate fruit set 5 consecutive years. No alternate bearing observed.

*Fertility.*—Self fertile.

*Density.*—Medium dense, usually pruned to vase shape to increase air movement and sunlight to enhance fruit color and health of fruit spurs.

*Hardiness.*—Hardy in all stone fruit growing areas of California. Tree grown in USDA Hardiness Zone 9. Winter chilling requirement approximately 300 hours at or below 45° F.

Trunk:

*Size.*—Medium, average circumference 25.4 cm at 22.9 cm above ground on a 6 year old tree.

*Stocky.*—Medium stocky.

*Texture.*—Medium shaggy, roughness increases with age.

*Color.*—Varies from 7.5YR 6/2 to 7.5YR 4/2.

Branches:

*Size.*—Medium. Average circumference 14.2 cm at 1.2 meters above ground. Crotch angle approximately 30°, increases with heavy crop load.

*Surface texture.*—New growth relatively smooth. Mature growth medium rough, roughness increases with age.

*Lenticels.*—Average number 24 in a 25.8 sq cm area. Average length 4.8 mm. Average width 2.1 mm. Color varies from 7.5YR 5/6 to 7.5YR 3/6.

*Color.*—New growth varies from 2.5GY 7/6 to 2.5GY 6/10. Mature growth varies from 7.5YR 3/8 to 7.5YR 2/4, varies with age of growth.

Leaves:

*Size.*—Large. Average length 128.4 mm. Average width 35.9 mm.

*Form.*—Elliptical.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 7.8 mm. Average width 1.8 mm. Longitudinally grooved. Surface — glabrous. Color varies from 5GY 7/6 to 5GY 7/8.

*Glands.*—Type — reniform. Size — small. Average length 1.0 mm. Average diameter 0.5 mm. Number varies from 1 to 3, average number 2. Located primarily on the base of leaf the blade and upper portion of petiole. Surface — glabrous. Color varies from 5YR 4/6 to 5YR 4/8.

*Stipules.*—None present at time of measurement.

*Color.*—Upper surface varies from 5GY 4/4 to 5GY 3/4. Lower surface varies from 5GY 5/4 to 5GY 4/4. Midvein color varies from 5GY 8/4 to 5GY 8/6.

Flower buds:

*Size.*—Large. Average length 19.7 mm. Average diameter 12.5 mm.

*Hardiness.*—Hardy with respect to California winters.

*Density.*—Dense.

*Form.*—Conical, becoming elongated before opening.

*Pedicel.*—Average length 7.5 mm. Average width 1.7 mm. Surface — glabrous. Color varies from 5RP 3/4 to 5GY 6/8.

*Color.*—Varies from 5RP 8/4 with 5RP 7/10.

Flowers:

*Blooming period.*—Date of First Bloom Feb. 23, 2023. Date of Petal Fall Mar. 5, 2023, varies slightly with climatic conditions.

*Size.*—Large. Average height 17.9 mm. Average diameter 40.8 mm.

*Petals.*—Number — normally five, alternately arranged to sepals. Size — large. Average length 22.9 mm. Average width 17.6 mm. Petal apex — rounded. Petal base — truncate. Form — elliptical. Arrangement — overlapping. Margin — sinuate. Both upper and lower surfaces glabrous. Color varies from 5RP 9/2 to 5RP 5/10, fades with age of flower.

*Sepals.*—Number — normally five, alternately arranged to petals. Size — large. Average length 7.1 mm. Average width 6.1 mm. Sepal apex — ovate. Shape — ovate to triangular. Margin — entire. Color — upper surface varies from 7.5RP 3/6 to 5GY 6/8. Lower surface varies from 5RP 5/4 to 5RP 2/8. Surface — upper surface glabrous, lower surface pubescent.

*Stamens.*—Average number per flower 40. Average filament length 12.1 mm. On average, the stamens are below the height of the petals. Filament color N 9.5/(white) to 5RP 5/10 as flower ages. Anther color varies from 2.5Y 8.5/4 to 5RP 3/8.

*Pollen.*—Present, self fertile. Color varies from 2.5Y 7/12 to 2.5Y 7/10.

*Pistil.*—Number — normally one. Average length 16.2 mm. Position of stigma an average of 1.2 mm above anthers. Surface — glabrous. Color varies from 5GY 8/4 to 5GY 6/8.

*Fragrance.*—Slight.

*Color.*—Varies from 5RP 9/2 to 5RP 7/8.

*Pedicel.*—Average length 6.9 mm. Average width 1.1 mm. Surface — glabrous. Color varies from 5RP 3/4 to 5GY 6/8.

*Number flowers per flower bud.*—Average number one.

Fruit:

*Maturity when described.*—Firm ripe and ready for consumption.

*Date of first picking.*—Jun. 1, 2023.

*Date of last picking.*—Jun. 11, 2023, varies slightly with climatic conditions.

*Size.*—Large. Average diameter axially 73.9 mm. Average transversely in suture plane 74.5 mm. Average weight 215.9 grams, varies slightly with fertility of the soil, amount of thinning and climatic conditions.

*Form.*—Globose.

*Suture.*—Nearly smooth, very slightly lipped.

*Ventral surface.*—Nearly smooth to slightly lipped.

*Apex.*—Slightly retuse.

*Base.*—Retuse.

*Stem cavity.*—Rounded to slightly elongated in suture plane. Average depth 11.3 mm. Average diameter 10.7 mm.

Stem:

*Size.*—Small to medium. Average length 12.8 mm. Average diameter 3.0 mm.

*Color.*—Varies from 5GY 6/8 to 5GY 5/6.

Flesh:

*Ripens.*—Evenly.

*Texture.*—Firm, meaty, crisp.

*Fibers.*—Few, small, tender.

*Firmness.*—Firm, comparable to other commercial nectarine varieties.

*Aroma.*—Moderate.

*Amydgalin.*—Undetected.

*Eating quality.*—Good.

*Flavor.*—Good, with a good balance between acid and sugar.

*Juice.*—Moderate amount, enhances flavor.

*Acidity.*—Not available.

*Brix.*—Average Brix 14.6°, varies slightly with amount of fruit per tree and climatic conditions.

*Color.*—Varies from 2.5Y 8/12 to 5Y 8/10 with 7.5R 3/12 near the apex.

*Pit cavity.*—Average length 36.3 mm. Average width 30.5 mm. Average depth 8.2 mm. Color varies from 5Y 8/10 to 2.5Y 8/12.

Skin:

*Thickness.*—Medium.

*Surface.*—Smooth.

*Pubesence.*—Wanting.

*Tendency to crack.*—None.

*Color.*—Ground color varies from 2.5Y 8/10 to 5Y 8/10. Overspread with 7.5R 4/12 to 7.5R 2/8.

Stone:

*Type.*—Clingstone, strong adherence to flesh.

*Size.*—Large. Average length 35.3 mm. Average width 29.5 mm. Average thickness 14.3 mm.

*Form.*—Obovoid.

*Base.*—Flat.

*Apex.*—Rounded.

*Surface.*—Pitted throughout, pits vary from rounded to elongated.

*Sides.*—Unequal, one side extending further outward from suture plane.

*Ridges.*—Relatively smooth, extending from base to apex.

*Tendency to split.*—None.

*Color.*—Varies from 5YR 5/6 to 5YR 5/8, when dry.

Kernel:

*Size.*—Medium to large. Average length 18.7 mm. Average width 12.8 mm. Average depth 5.2 mm.

*Form.*—Ovate.

*Viability.*—Viable, complete embryo development.

*Skin color.*—Varies from 5Y 9/4 to 5Y 9/6.

Use: Dessert. Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

PLANT/FRUIT DISEASE RESISTANCE/SUSCEPTIBILITY

No specific testing for relative plant/fruit disease resistance/susceptibility has been designed. Under close observation during planting, growing and harvesting of fruit, under normal cultural and growing conditions near Modesto, California, no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of nectarine tree (*Prunus persica* var. *nucipersica*), substantially as illustrated and described.

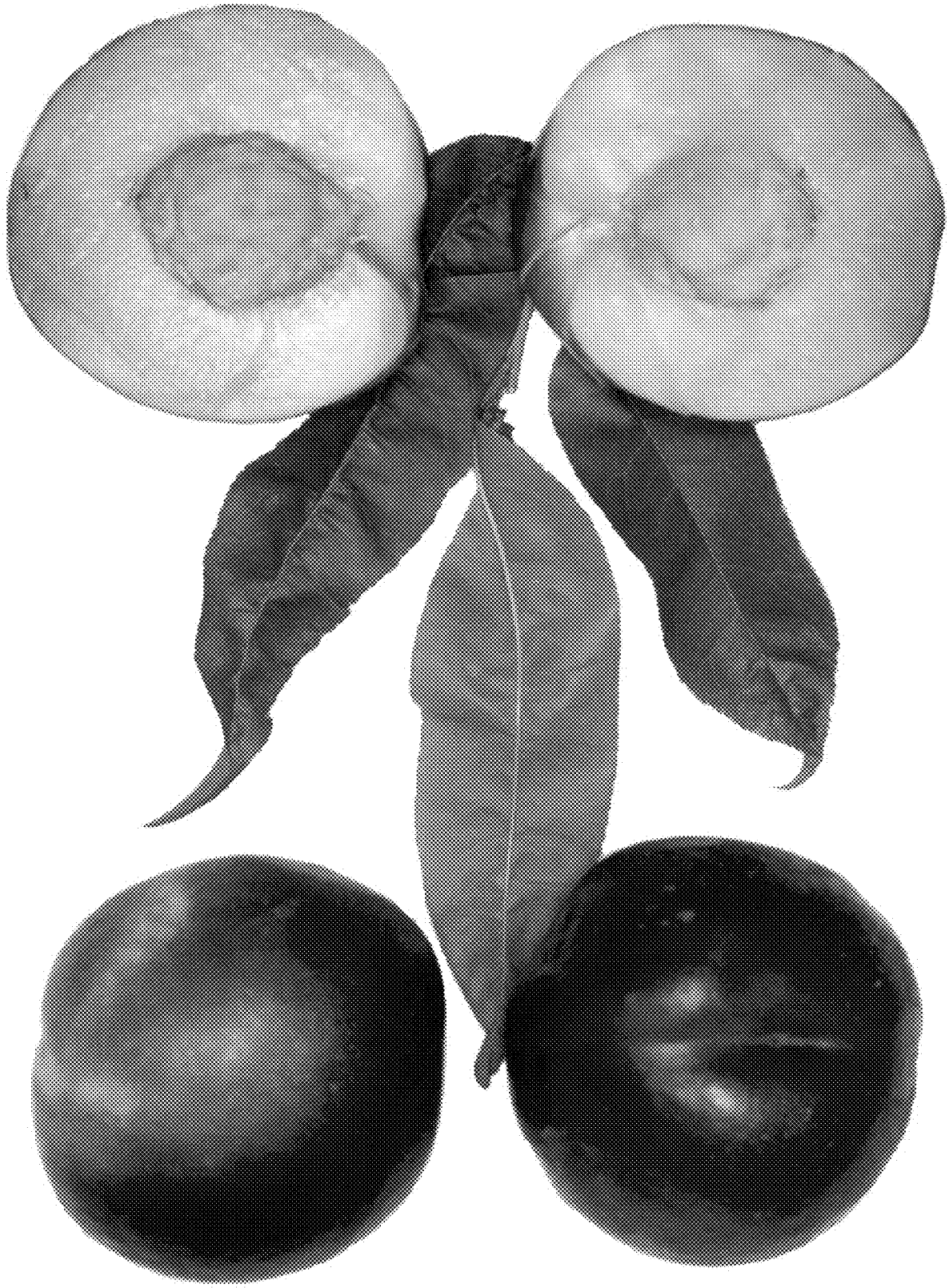

* * * * *